US00PP13629P2

(12) United States Plant Patent
Oliver

(10) Patent No.: US PP13,629 P2
(45) Date of Patent: Mar. 4, 2003

(54) TIARELLA PLANT NAMED 'BUTTERFLY WINGS'

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 0 days.

(21) Appl. No.: 10/014,462

(22) Filed: Dec. 8, 2001

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—June Hwu
(74) *Attorney, Agent, or Firm*—C. A. Whealy

(57) ABSTRACT

A new and distinct cultivar of Tiarella plant named 'Butterfly Wings', characterized by its dense and mounded plant habit; palmately lobed green-colored leaves with dark red purple central blotch; leaves simple or compound with development; numerous light pink showy flowers arranged on dense racemes; and excellent garden performance.

1 Drawing Sheet

BOTANICAL CLASSIFICATION/CULTIVAR DESIGNATION

*Tiarella cordifolia* cultivar Butterfly Wings.

BACKGROUND OF THE INVENTION

The present invention relates to a new and distinct cultivar of Tiarella plant, botanically known as *Tiarella cordifolia* and hereinafter referred to by the name 'Butterfly Wings'.

The new Tiarella is a product of a planned breeding program conducted by the Inventor in Scottdale, Pa. The objective of the breeding program is to create new Tiarella cultivars having interesting leaf shape and attractive flower and leaf coloration.

The new Tiarella was discovered by the Inventor in a controlled environment in Scottdale, Pa., from seedling progeny from a cross-pollination made by the Inventor in May, 1997, of the Tiarella cultivar Adagio, not patented, as the female, or seed, parent with an unidentified selection of *Tiarella cordifolia*, not patented, as the male, or pollen, parent. The new Tiarella was selected by the Inventor in June, 1998. The selection of this plant was based on its desirable leaf shape and coloration.

Asexual reproduction of the new Tiarella by cuttings taken in a controlled environment in Scottdale, Pa., since May, 1999, has shown that the unique features of this new Tiarella are stable and reproduced true to type in successive generations.

SUMMARY OF THE INVENTION

The cultivar Butterfly Wings has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Butterfly Wings'. These characteristics in combination distinguish 'Butterfly Wings' as a new and distinct cultivar:

1. Full and densely foliated; mounded plant habit.
2. Palmately lobed green-colored leaves with dark red purple central blotch; leaves simple or compound with development.

3. Numerous light pink showy flowers arranged on dense racemes.
4. Excellent garden performance.

Plants of the new Tiarella can be compared to plants of the female parent, the cultivar Adagio. In side-by-side comparisons conducted by the Inventor in Scottdale, Pa., plants of the new Tiarella differed from plants of the cultivar Adagio in the following characteristics:

1. Leaves of plants of the new Tiarella were smooth whereas leaves of plants of the cultivar Adagio were rugose or "quilted".
2. Leaves of plants of the new Tiarella had angled lobes whereas leaves of plants of the cultivar Adagio had rounded lobes.
3. Plants of the new Tiarella had simple and compound leaves whereas plants of the cultivar Adagio only had simple leaves.

Plants of the new Tiarella differed primarily from plants of the male parent, the unidentified Tiarella selection, in leaf shape.

Plants of the new Tiarella can be compared to plants of the cultivar Elizabeth Oliver, not patented. In side-by-side comparisons conducted by the Inventor in Scottdale, Pa., plants of the new Tiarella differed from plants of the cultivar Elizabeth Oliver in the following characteristics:

1. Plants of the new Tiarella had smaller leaves than plants of the cultivar Elizabeth Oliver.
2. Upper leaf surfaces of plants of the new Tiarella had dark red purple central blotches whereas upper leaf surfaces of plants of the cultivar Elizabeth Oliver had dark red purple markings mostly along the main veins.
3. Plants of the new Tiarella had simple and compound leaves whereas plants of the cultivar Elizabeth Oliver only had simple leaves.
4. Plants of the new Tiarella were not as freely flowering as plants of the cultivar Elizabeth Oliver.

Plants of the new Tiarella can also be compared to plants of the cultivar Tiger Stripe, not patented. In side-by-side comparisons conducted by the Inventor in Scottdale, Pa., plants of the new Tiarella differed from plants of the cultivar Tiger Stripe in the following characteristics:

1. Plants of the new Tiarella were shorter than plants of the cultivar Tiger Stripe.
2. Plants of the new Tiarella had smaller leaves with shorter petioles than plants of the cultivar Tiger Stripe.

3. Upper leaf surfaces of plants of the new Tiarella had dark red purple central blotches whereas upper leaf surfaces of plants of the cultivar Tiger Stripe had irregular dark purple markings.
4. Plants of the new Tiarella had simple and compound leaves whereas plants of Tiger Stipe only had simple leaves.

BRIEF DESCRIPTION OF THE PHOTOGRAPH

The accompanying colored photograph illustrates the overall appearance of the new Tiarella, showing the colors as true as it is reasonably possible to obtain in colored reproductions of this type. Colors in the photograph may differ slightly from the color values cited in the detailed botanical description which accurately describe the colors of the new Tiarella. The photograph comprises a side perspective view of a typical flowering plant of 'Butterfly Wings' that was about one year old and grown in the landscape.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Scottdale, Pa. in a glass-covered greenhouse and under cultural conditions which approximate commercial practice. Plants were grown as single plants in one-gallon containers and were about one year old. During the production of the plants, day temperatures ranged from 15 to 26° C. and night temperatures ranged from 5 to 15° C. Measurements and numerical values represent averages taken from a group of flowering plants.

Botanical classification: *Tiarella cordifolia* cultivar Butterfly Wings.

Parentage:

*Female, or seed, parent.*—*Tiarella cordifolia* cultivar Adagio, not patented.

*Male, or pollen, parent.*—Unidentified selection of *Tiarella cordifolia,* not patented.

Propagation:

*Type.*—By cuttings.

*Time to initiate roots, summer and winter.*—About 14 days at 23° C.

*Time to produce a rooted cutting, summer and winter.*—About 30 days at 23° C.

*Root description.*—Fine, fibrous and well-branched.

Plant description:

*Appearance.*—Perennial; basal rosette plant habit with leaves developing from the base; densely foliated; full, mounded plant habit with upright racemes with showy light pink-colored flowers. Vigorous and robust growth habit.

*Plant size.*—Height: Soil level to top of foliar plane: About 13.5 cm. Soil level to top of panicles: About 27.5 cm. Diameter or spread: About 22.5 cm.

*Foliage description.*—Arrangement: Basal rosette; young leaves, simple; developed leaves, compound with three leaflets. Length: About 6 cm. Width: About 5.5 cm. Shape: Cordate; deeply palmately lobed. Apex: Acute. Base: Auriculate. Margin: Crenate with fine ciliation; deeply lobed. Texture, upper and lower surfaces: Slightly rough; slightly pubescent. Venation pattern: Palmate. Color: Developing and fully expanded leaves, upper surface: 144A to 143B; central blotch, 59A. Developing and fully expanded leaves, lower surface: 144B. Venation, upper and lower surface: Same as lamina. Petiole: Length: About 10 cm. Diameter: About 1.4 mm. Texture, upper and lower surfaces: Pubescent. Color, upper and lower surfaces: Towards leaf, 144B; towards base of plant, 59C.

Flower description:

*Appearance/arrangement.*—Single campanulate flowers arranged on numerous erect, dense and cylindrical racemes; about 30 to 90 flowers and flower buds per flowering stem. Flowers face mostly outward to slightly upright. Flowering continuous with about ten flowering stems per plant developing throughout the flowering period. Flowers persistent. Flowers fragrant, sweet.

*Time of flowering.*—Under natural conditions, plants flower during May and June in Scottdale, Pa.

*Inflorescence longevity.*—Individual inflorescences last about one week on the plant.

*Inflorescence size.*—Length: About 7–8 cm. Diameter: About 2.5 cm.

*Flower size.*—Diameter: About 8 mm. Depth (height): About 5 mm.

*Flower buds.*—Height: About 3 mm. Diameter: About 2.5 mm. Shape: Bulbous. Color, at stage of showing color: 57D.

*Petals.*—Quantity/arrangement: Five petals; radially symmetrical; fused at base. Length: About 4 mm. Width: About 0.9 mm. Shape: Spatulate. Apex: Acute. Margin: Entire. Texture: Smooth. Color: When opening and fully opened, upper surface: Close to 155D. When opening and fully opened, lower surface: 62D.

*Sepals.*—Quantity/arrangement: Five sepals; radially symmetrical; fused at base. Length: About 3.5 mm. Width: About 1 mm. Shape: Oval. Apex: Obtuse. Margin: Entire. Texture: Pubescent. Color: When opening and fully opened, upper surface: Close to 155D. When opening and fully opened, lower surface: Close to 155D overlain with scattered red purple, 57D, hairs.

*Peduncle.*—Strength: Strong; flexible. Aspect: Mostly upright to slightly angled outwardly to 30° from vertical. Length: About 25–30 cm. Diameter: About 1.2 mm. Texture: Smooth. Color: 144B underlain with 57D.

*Pedicels.*—Strength: Strong; wiry. Aspect: About 10 to 30° from vertical. Length: About 4 cm. Diameter: About 0.5 mm. Texture: Pubescent. Color: 144B underlain with 57D.

*Reproductive organs.*—Androecium: Stamen number: Five per flower. Anther shape: Oval. Anther length: About 0.2 mm. Anther color: 25B. Amount of pollen: Moderate. Pollen color: 16B. Gynoecium: Pistil number: One per flower. Pistil length: About 5 mm. Stigma shape: Rounded. Stigma color: 157C. Style length: About 3 mm. Style color: 157C. Ovary color: 157C.

*Seed.*—Amount: Abundant. Length: About 0.8 mm. Diameter: About 0.6 mm. Color: Close to 202A.

Disease/pest resistance: Resistance to pathogens and pests common to Tiarella has not been observed on plants grown under commercial conditions.

Temperature tolerance: Plants of the new Tiarella have demonstrated good tolerance to night temperatures as low as −35° C. and day temperatures as high as 40° C.

It is claimed:

1. A new and distinct cultivar of Tiarella plant named 'Butterfly Wings', as illustrated and described.

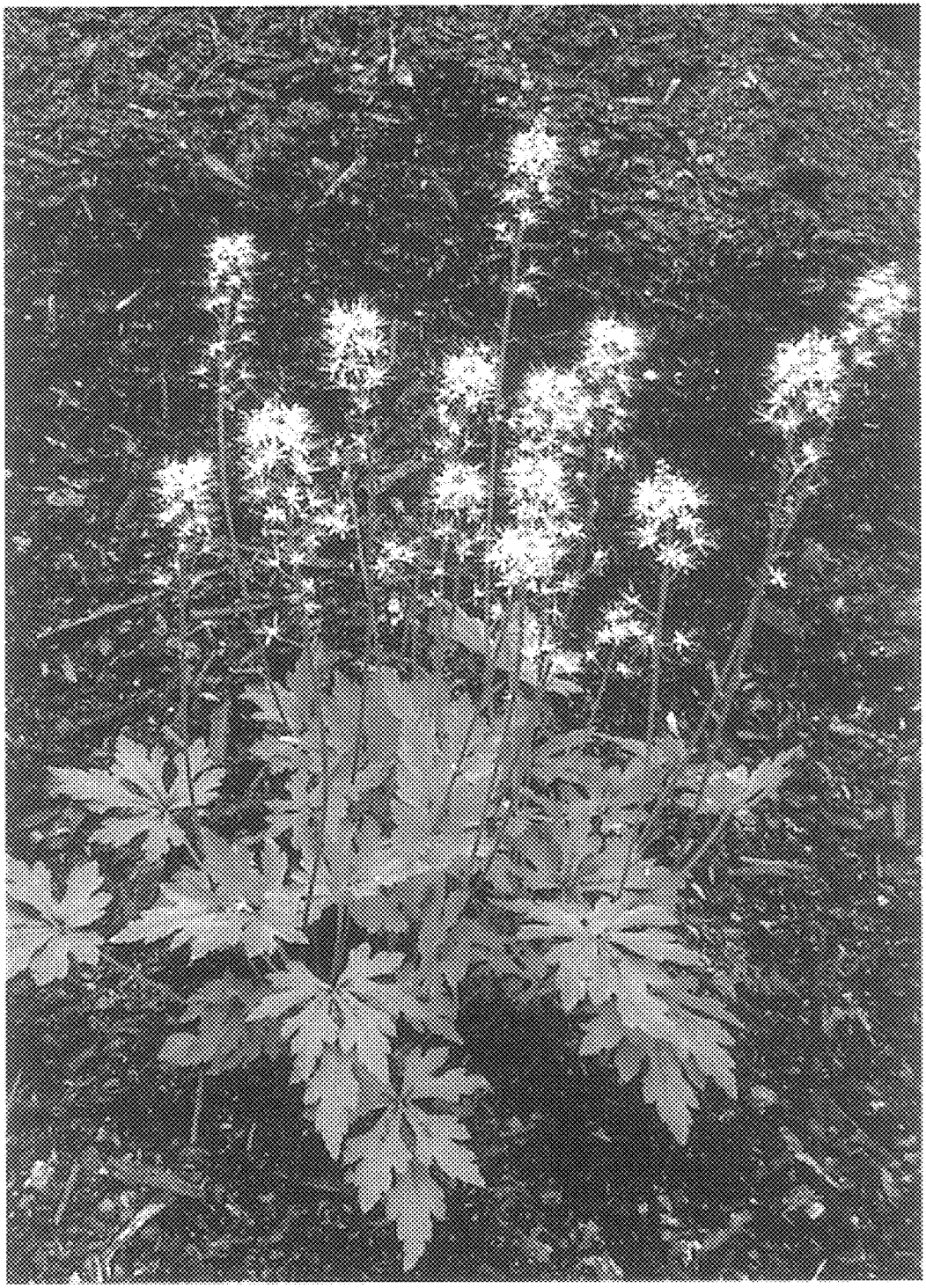

* * * * *